United States Patent
Fujitani

(10) Patent No.: US 10,182,701 B2
(45) Date of Patent: Jan. 22, 2019

(54) ELECTRONIC ENDOSCOPE SYSTEM WITH ROTATION ANGLE CALCULATION OF INSERTION PORTION

(71) Applicant: OLYMPUS CORPORATION, Tokyo (JP)

(72) Inventor: Kiwamu Fujitani, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 1009 days.

(21) Appl. No.: 14/459,390

(22) Filed: Aug. 14, 2014

(65) Prior Publication Data

US 2014/0357947 A1 Dec. 4, 2014

Related U.S. Application Data

(63) Continuation of application No. PCT/JP2013/062363, filed on Apr. 26, 2013.

(30) Foreign Application Priority Data

May 23, 2012 (JP) .................................. 2012-117770

(51) Int. Cl.
*A61B 1/00* (2006.01)
*A61B 1/05* (2006.01)
(Continued)

(52) U.S. Cl.
CPC ........ *A61B 1/00096* (2013.01); *A61B 1/0005* (2013.01); *A61B 1/00006* (2013.01);
(Continued)

(58) Field of Classification Search
CPC ............ A61B 1/00006; A61B 1/00096; A61B 1/00071; A61B 1/0005; A61B 1/0052;
(Continued)

(56) References Cited

U.S. PATENT DOCUMENTS

2004/0267093 A1* 12/2004 Miyagi .............. A61B 1/00039 600/146
2010/0076263 A1* 3/2010 Tanaka ............... A61B 1/00006 600/109

(Continued)

FOREIGN PATENT DOCUMENTS

EP 2 070 465 A1 6/2009
EP 2 215 960 A1 8/2010
(Continued)

OTHER PUBLICATIONS

Extended Supplementary European Search Report dated Oct. 16, 2015 from related European Application No. 13 79 3702.5.
(Continued)

*Primary Examiner* — John P Leubecker
*Assistant Examiner* — William Chou
(74) *Attorney, Agent, or Firm* — Scully, Scott, Murphy & Presser, P.C.

(57) ABSTRACT

An electronic endoscope system including: an operation portion; an insertion portion including on a distal end side thereof a bending portion, and connected to the operation portion so as to be rotatable with respect to the operation portion, a bending direction of the bending portion changing depending on the rotation; an image pickup device disposed in the insertion portion, for generating an image of a subject; a physical quantity generation portion that generates a physical quantity which changes depending on the rotation of the insertion portion; a detection portion that detects and outputs the physical quantity generated by the physical quantity generation portion; a rotation angle calculation portion that receives the physical quantity outputted from the detection portion and calculates a rotation angle of the insertion portion; and a display portion that displays the (Continued)

image of the subject and information corresponding to the rotation angle of the insertion portion.

13 Claims, 12 Drawing Sheets

(51) Int. Cl.
    *A61B 1/06*         (2006.01)
    *G02B 23/26*      (2006.01)
    *G02B 23/24*      (2006.01)
    *A61B 1/005*     (2006.01)

(52) U.S. Cl.
    CPC .......... *A61B 1/0052* (2013.01); *A61B 1/0055* (2013.01); *A61B 1/00071* (2013.01); *G02B 23/2476* (2013.01); *G02B 23/26* (2013.01)

(58) Field of Classification Search
    CPC ... A61B 1/0055; G02B 23/2476; G02B 23/26
    USPC ....... 600/102, 103, 109, 117, 118, 137, 139, 600/140, 141, 145, 146, 160
    See application file for complete search history.

(56) References Cited

U.S. PATENT DOCUMENTS

| | | |
|---|---|---|
| 2011/0275896 A1 | 11/2011 | Tanaka |
| 2011/0295063 A1 | 12/2011 | Umemoto et al. |

FOREIGN PATENT DOCUMENTS

| | | |
|---|---|---|
| JP | 01-302216 A | 12/1989 |
| JP | H03-037034 A | 2/1991 |
| JP | 09-299329 A | 11/1997 |
| JP | 2005-254002 A | 9/2005 |
| JP | 2009-050540 A | 3/2009 |
| JP | 2010-234058 A | 10/2010 |

OTHER PUBLICATIONS

International Search Report dated Jul. 16, 2013 issued in PCT/JP2013/062363.

European Patent Office Communication dated Apr. 3, 2018 in corresponding European Patent Application No. 13 793 702.5.

\* cited by examiner

ELECTRONIC ENDOSCOPE SYSTEM WITH ROTATION ANGLE CALCULATION OF INSERTION PORTION

CROSS REFERENCE TO RELATED APPLICATION

This application is a continuation application of PCT/JP2013/062363 filed on Apr. 26, 2013 and claims benefit of Japanese Application No. 2012-117770 filed in Japan on May 23, 2012, the entire contents of which are incorporated herein by this reference.

BACKGROUND OF THE INVENTION

1. Field of the Invention

The present invention relates to an electronic endoscope system including an endoscope having an insertion portion configured to be rotatable with respect to an operation portion.

2. Description of the Related Art

Conventionally, endoscopes having an insertion portion configured to rotate with respect to an operation portion have been proposed. Such an endoscope is provided with an insertion portion rotating dial, for example, at an operator's hand side of the insertion portion of the endoscope, and the insertion portion is configured to rotate through rotating operation of the insertion portion rotating dial.

Specifically, Japanese Patent Application Laid-Open Publication No. 2005-254002, for example, discloses a configuration in which an insertion portion rotating portion (21) which rotates integrally with an insertion portion (2) is provided, and the insertion portion (2) can be moved rotationally with respect to an operation portion (3) through twisting operation of the insertion portion rotating portion (21).

In such a configuration, an operator inserts an insertion portion of an endoscope into a subject while rotating an insertion portion rotating dial, as necessary. At this time, the operator confirms the rotation angle of the insertion portion by visually checking the insertion portion rotating dial.

When the endoscope is an electronic endoscope, the operator operates the endoscope while checking an image obtained from the electronic endoscope on a monitor.

Therefore, the operator views the monitor when performing insertion operation, and looks away from the monitor to visually check the insertion portion rotating dial when confirming the rotation angle of the insertion portion, that is, it has been necessary for the operator to change his or her line of sight.

In order to address such a problem, Japanese Patent Application Laid-Open Publication Nos. 2010-234058 and 2009-50540, for example, disclose an endoscope capable of rotating an insertion portion (12) with respect to an operation portion (16) through rotation operation of a rotation knob (19), wherein a cover indicator (27) and a knob indicator (36) are provided to a cover (25) of an operation portion housing (23) and a rotation knob (19) on a proximal end side of the insertion portion (12), respectively. According to such a configuration, when the knob indicator (36) is brought into line with the cover indicator (27), the operator can recognize that the insertion portion (12) is in the neutral position with respect to the operation portion (16). Furthermore, these publications recite a technique for providing a force amount changing mechanism for changing a rotation force amount required for rotation depending on the rotation angle of the insertion portion (12). Such a mechanism enables the operator to force-sensitively perceive the rotation angle of the insertion portion (12). Therefore, according to the technique recited in these publications, whether the rotation angle of the insertion portion is in the neutral position or not can be confirmed by visual check and perceived by the operator sensing the force amount.

SUMMARY OF THE INVENTION

An electronic endoscope system according to an aspect of the present comprising: an operation portion configured to be operable by an operator; an insertion portion including on a distal end side thereof a bending portion, the insertion portion being connected to the operation portion so as to be rotatable with respect to the operation portion, a bending direction of the bending portion changing depending on the rotation; an image pickup device disposed in the insertion portion and configured to generate an electronic image by photoelectrically converting an optical image of a subject; a physical quantity generation portion configured to generate a physical quantity which changes depending on the rotation of the insertion portion; a detection portion configured to detect the physical quantity generated by the physical quantity generation portion and output the detected physical quantity; a rotation angle calculation portion configured to receive the physical quantity outputted from the detection portion and calculate a rotation angle of the insertion portion; and a display portion configured to display the image of the subject generated by the image pickup device and information generated based on the calculated rotation angle, the information corresponding to the rotation angle of the insertion portion.

DETAILED DESCRIPTION OF THE PREFERRED EMBODIMENT(S)

Hereinafter, embodiments of the present invention will be described with reference to drawings.

[First Embodiment]

Figure 1:
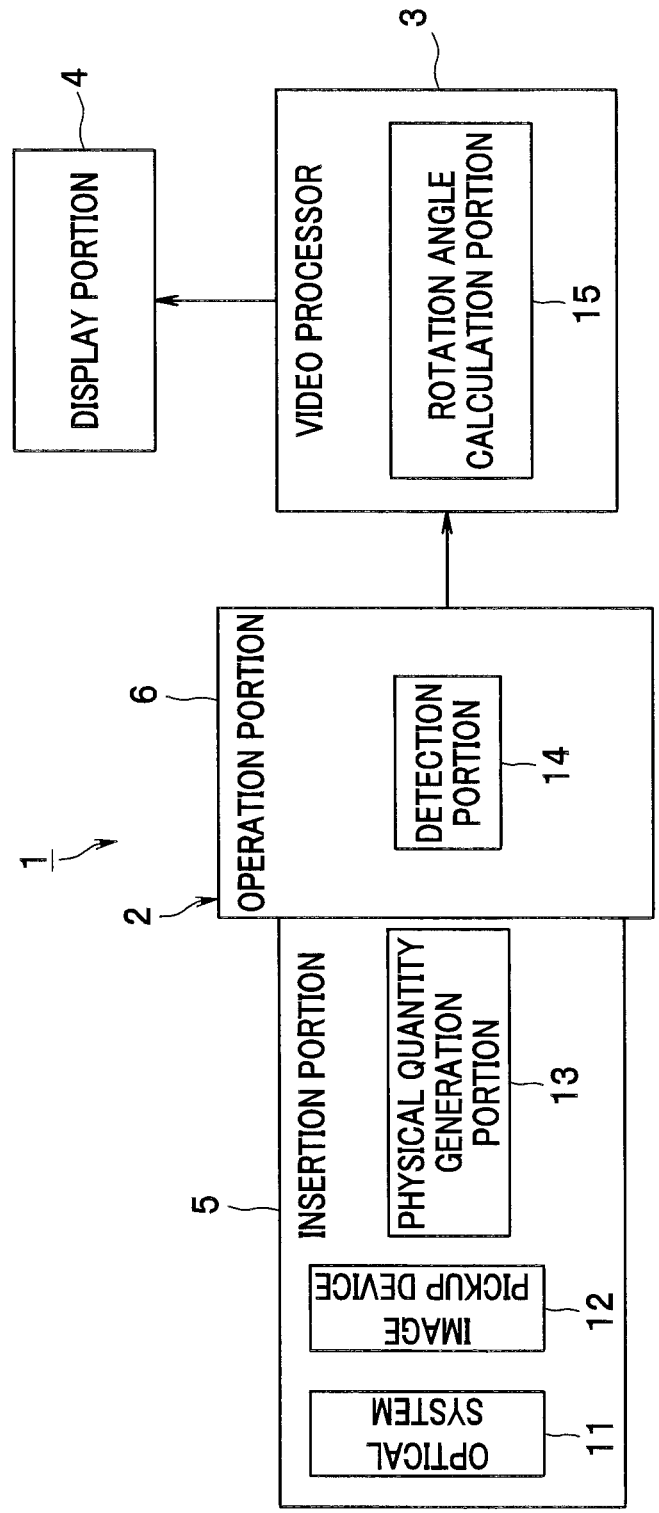
FIG. 1 is a block diagram showing a configuration of an electronic endoscope system according to a first embodiment of the present invention.

FIGS. 1 to 6 show the first embodiment of the present invention, and FIG. 1 is a block diagram showing a configuration of an electronic endoscope system.

As shown in FIG. 1, an electronic endoscope system 1 includes an electronic endoscope (hereinafter, just referred to as endoscope) 2, a video processor 3, and a display portion 4.

The endoscope 2 includes an operation portion 6 on an operator's hand side, which is configured to be held and operated by the operator, and an elongated insertion portion 5 provided so as to be extended from the operation portion 6 toward distal end side.

The insertion portion 5 is configured to be rotatable about a central axis O (the central axis of the insertion portion 5, See FIG. 3, etc.) with respect to the operation portion 6. The insertion portion 5 includes an optical system 11 configured by an objective lens and the like, an image pickup device 12 that photoelectrically converts an optical image of a subject which is formed by the optical system 11 to generate an electronic image, a physical quantity generation portion 13 that generates a physical quantity that changes depending on a rotation angle of the insertion portion 5 with respect to the operation portion 6. In the present embodiment, the physical quantity generation portion 13 is a deformation portion which is formed such that the shape about the central axis O changes depending on an angle about the central axis O, as described below.

In addition, the operation portion 6 is provided with a detection portion 14 that detects a physical quantity generated by the physical quantity generation portion 13. Note that, in the present embodiment or other embodiments, the "physical quantity" means a measurable attribute of a phenomenon or a substance.

The video processor 3 processes an image picked up by the image pickup device 12. The video processor 3 is provided with a rotation angle calculation portion 15 that calculates a rotation angle value corresponding to the rotation angle of the insertion portion 5, on the basis of the physical quantity detected by the detection portion 14. However, the arranging position of the rotation angle calculation portion 15 is not limited to inside the video processor 3.

Figure 6:
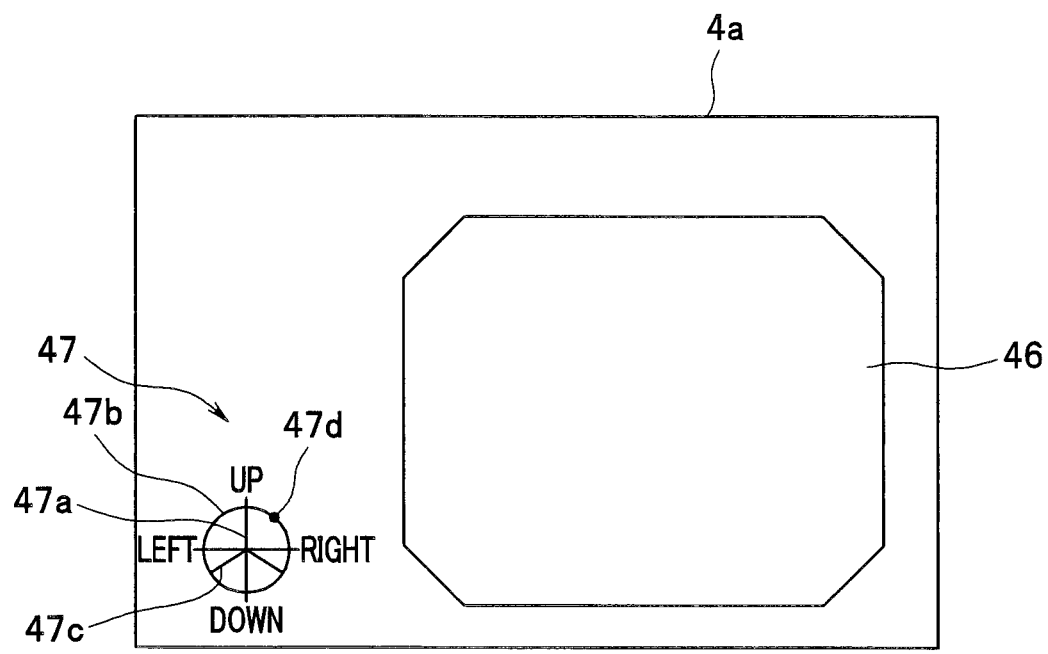
FIG. 6 illustrates a display example of an endoscopic image and a rotation angle display image on a display portion according to the first embodiment.

A display portion 4 includes a monitor, for example, and displays an endoscopic image 46 (See FIG. 6) of a subject, which has been processed in the video processor 3, and also displays an image indicating the rotation angle (a rotation angle display image 47 as shown in FIG. 6, for example) of the insertion portion 5 with respect to the operation portion 6 on the basis of the rotation angle value calculated by the rotation angle calculation portion 15.

Figure 2:
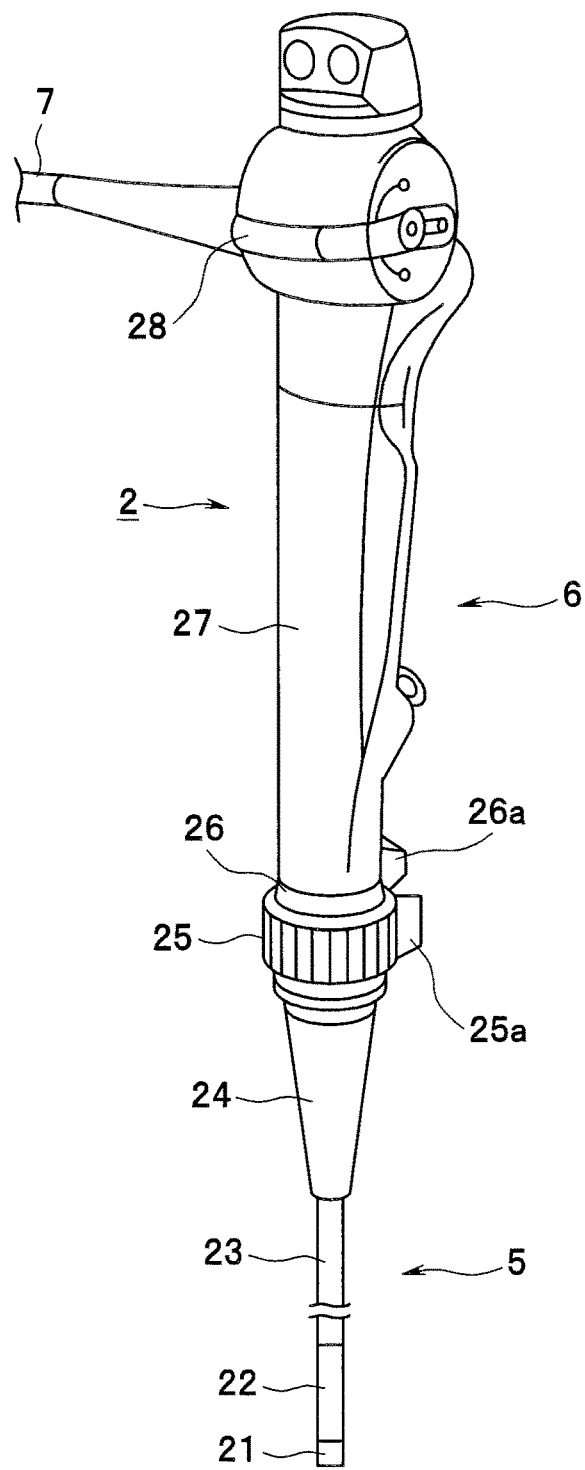
FIG. 2 is a perspective view showing a configuration of an endoscope according to the first embodiment.

Next, FIG. 2 is a perspective view showing the configuration of the endoscope 2.

As shown in FIG. 2, the insertion portion 5 includes, in the following order from the distal end side: a distal end rigid portion 21; a bending portion 22 that is bendable in two directions, i.e., one direction and in a direction opposite to the one direction; a flexible tube portion 23 that is long and flexible; and a bend preventing portion 24 having a tapered shape. The optical system 11 and image pickup device 12 are disposed in the distal end rigid portion 21 among the portions described above. In addition, the bend preventing portion 24 is provided at a proximal end portion of the insertion portion 5, for preventing flexure of the insertion portion 5 with respect to the operation portion 6.

At a connecting part of the insertion portion 5 and the operation portion 6 located on the proximal end side of the insertion portion, an insertion portion rotating dial 25 having an annular shape and having a knurling formed on a circumferential surface thereof. The insertion portion rotating dial 25 is configured to rotationally move integrally with the insertion portion 5. When the operator rotationally operates the insertion portion rotating dial 25, the insertion portion 5 is rotated with respect to the operation portion 6. Bending of the bending portion 22 after adjustment of the rotation angle of the insertion portion 5 to a desired rotation angle enables the bending operation in a desired direction.

A knob convex portion 25a is arranged so as to protrude from a part of the circumferential direction of the insertion portion rotating dial 25 in an outer radial direction. The knob convex portion 25a is an indicator for positioning the insertion portion 5 in a neutral position with respect to the operation portion 6 by aligning the position of the knob convex portion with a position of an UP bending indicator 26a provided so as to protrude from a predetermined position in the circumferential direction of an indicator ring 26 located on the distal end side of the operating portion 6. The neutral position is the position where the bending operation direction of a bending lever 28 which is a bending operation portion coincides with the bending direction of the bending portion 22. Note that another indicator (for example, a scale, etc.) may be provided to each of the knob convex portion 25a and the UP bending indicator 26 for more accurate alignment.

The operation portion 6 includes a grasping portion 27 configured to be grasped by the operator, and, for example, the rotational operation type bending lever 28 which can be operated for bending with the thumb of the hand grasping the grasping portion 27. The bending operation through the rotation of the bending lever 28 causes the bending portion 22 to perform bending action.

In addition, a universal cable 7 is extended from the proximal end portion of the operation portion 6, to be connected to the video processor 3 or a light source apparatus, etc., not shown.

Figure 3:
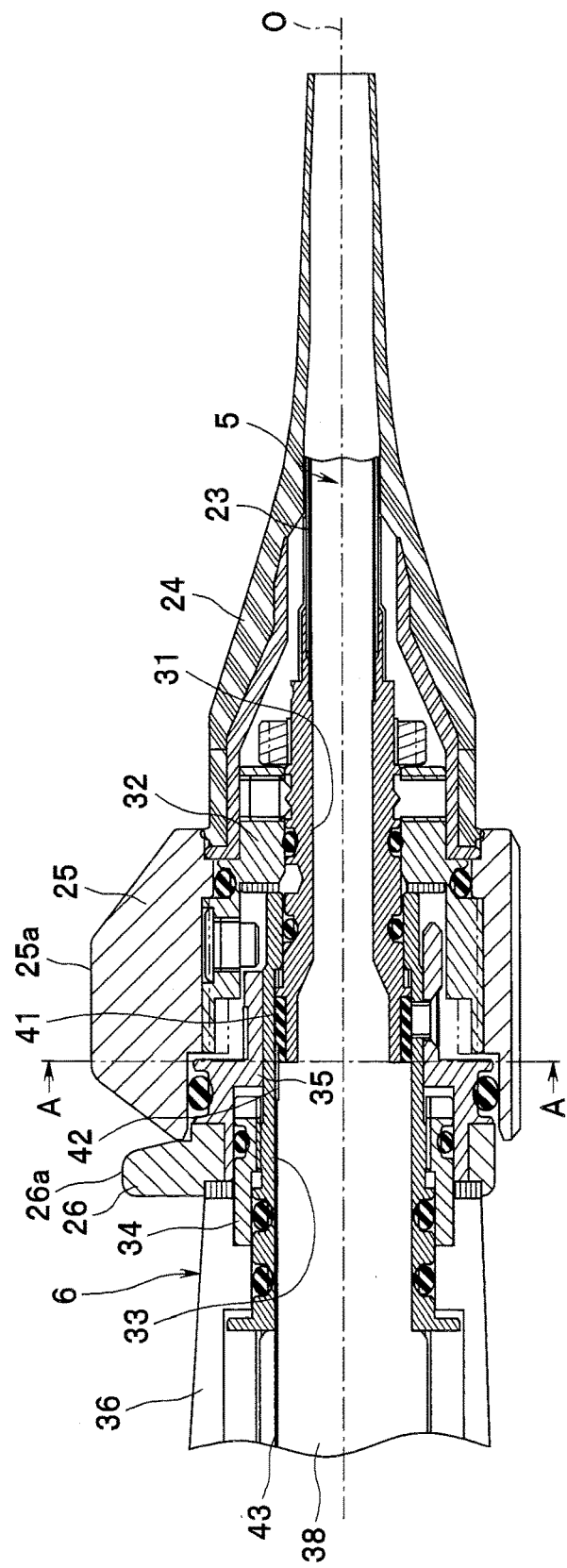
FIG. 3 is a cross-sectional view of a connecting part of an operation portion and an insertion portion according to the first embodiment, taken along an axial direction.

FIG. 3 is a cross-sectional view of the connecting part of the operation portion 6 and the insertion portion 5, taken along the axial direction.

At the proximal end portion of the flexible tube portion 23 of the insertion portion 5, a cylindrical insertion portion collet 31 is disposed so as to protrude toward the proximal end side in the direction of the central axis O. In addition, an insertion portion housing 32 is disposed on the outer circumferential side of the insertion portion collet 31. On the outer circumferential side of the insertion portion housing 32, the above-described insertion portion rotating dial 25 is disposed. The bend preventing portion 24 is disposed on the distal end side of the insertion portion rotating dial 25.

On the other hand, at the distal end portion inside the operation portion 6, a cylindrical operation portion collet 33 is disposed so as to protrude toward the distal end side in the direction of the central axis O. The proximal end portion of the insertion portion collet 31 is fitted into the cylindrical inner part of the distal end portion of the operation portion collet 33 so as to be rotatable about the central axis O (hereinafter the fitting part of the operation portion collet 33 and the insertion portion collet 31 is referred to as a collet fitting portion).

In addition, an operation portion exterior armor 36 is disposed on the outer circumference on the proximal end side of the operation portion collet 33.

Furthermore, a first ring-shaped member 34 is disposed on the outer circumference of the operation portion collet 33 at a substantially middle position in the direction of the central axis O, so as to be pressed by the operation portion exterior armor 36. The indicator ring 26 is outwardly fitted and fixed to the first ring-shaped member via a second ring-shaped member 35.

Note that an endoscope inner portion 38 in which various signal cables, forceps channels, and the like are disposed is configured to be watertight from outside even at the connecting part of the operation portion 6 and the insertion portion 5 by using a plurality of O-rings and the like.

Figure 4:
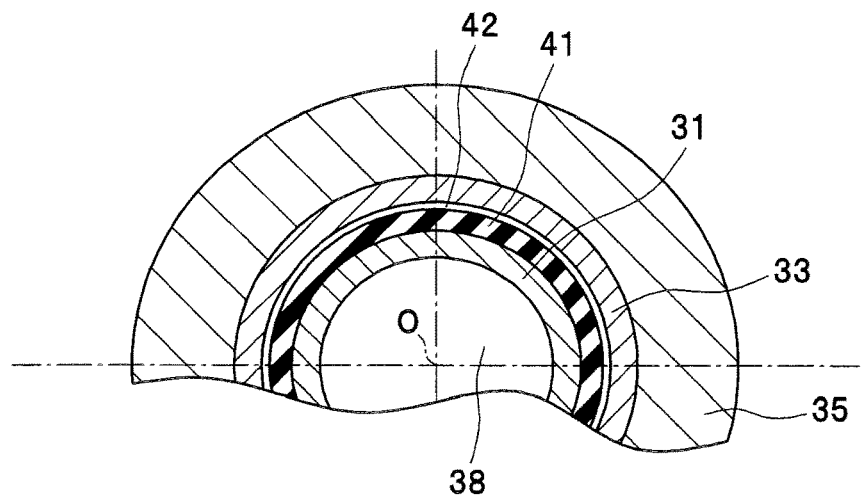
FIG. 4 illustrates a part of a cross section taken along the A-A line in FIG. 3 according to the first embodiment.
Figure 5:
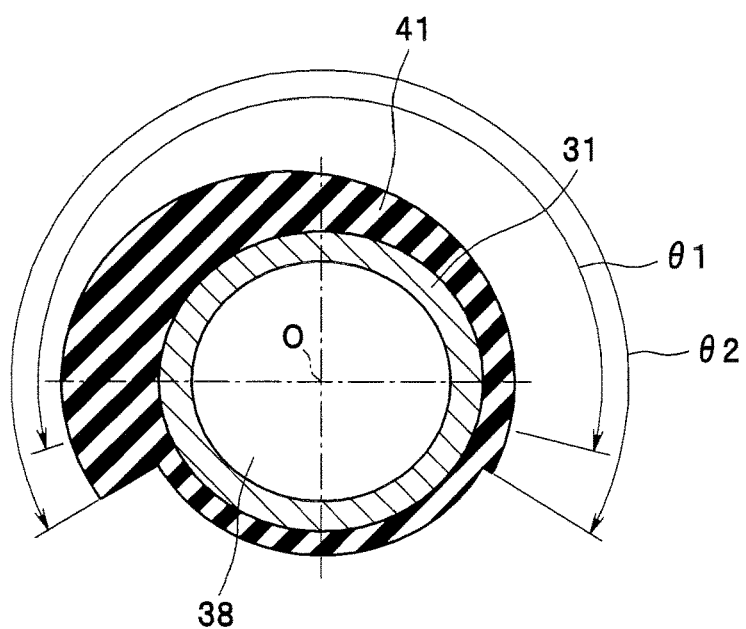
FIG. 5 illustrates a cross-sectional shape of a deformation portion provided on an outer circumference of an insertion portion collet according to the first embodiment in an exaggerated manner.

Next, description will be made on the configuration of the collet fitting portion with reference to above-described FIGS. 3, 4 and 5. FIG. 4 illustrates a part of the cross section taken along the A-A line in FIG. 3, and FIG. 5 illustrates the cross-sectional shape of the deformation portion provided on the outer circumference of the insertion portion collet 31 in an exaggerated manner On the inner circumference of the collet fitting portion of the operation portion collet 33, a sheet-like pressure sensor 42 is disposed as the detection portion 14 in a relatively narrow range in the circumferential direction. A signal line 43 is disposed from the pressure sensor 42 toward the proximal end side, and the signal line 43 is electrically connected to the rotation angle calculation portion 15 in the video processor 3 via the universal cable 7.

The deformation portion 41 whose outer diameter shape about the central axis O is uneven is provided as the physical quantity generation portion 13 as shown in FIG. 1, on the outer circumference of the collet fitting portion of the insertion portion collet 31 at a position where the deformation portion can contact the pressure sensor 42. Specifically, as shown in FIG. 5, the deformation portion 41 is formed by an elastic material such that the diameter about the central axis O of the insertion portion 5 changes depending on the angle about the central axis O (for example, the outside contour of the cross section perpendicular to the central axis O becomes a spiral shape). Note that an angular range $\theta 2$ in the circumferential direction, within which the outer diameter shape of the deformation portion 41 is changed, includes an angular range $\theta 1$ within which the deformation portion 41 can contact the pressure sensor 42 (the angular range $\theta 1$ is substantially equal to the angular range within which the insertion portion 5 can be rotated with respect to the operation portion 6).

According to such a configuration, when the rotation angle of the insertion portion 5 with respect to the operation portion 6 is changed, the deformation portion 41 applies different pressure depending on the rotation angle to the pressure sensor 42 (that is, the physical quantity generated by the deformation portion 41 as the physical quantity generation portion 13 so as to change depending on the rotation angle of the insertion portion 5 with respect to the operation portion 6 is pressure). More specifically, when a small-diameter part of the deformation portion 41 contacts the pressure sensor 42, the pressure to be applied to the pressure sensor 42 is small, and as the diameter of the deformation portion becomes larger, a larger pressure is applied to the pressure sensor 42. As a result, the pressure detected by the pressure sensor 42 changes depending on the rotation angle of the insertion portion 5. The pressure sensor 42 sends the pressure thus detected to the rotation angle calculation portion 15.

The rotation angle calculation portion 15 calculates the rotation angle of the insertion portion 5 based on the pressure received from the pressure sensor 42.

FIG. 6 illustrates a display example of the endoscopic image 46 and the rotation angle display image 47 on the display portion 4.

The video processor 3 uses up, down, left and right positions about the central axis O of the insertion portion 5 as coordinates and generates rotation angle display image data in which an indicator showing the rotation angle of the insertion portion 5 is superimposed on the coordinates, based on the rotation angle calculated by the rotation angle calculation portion 15.

As described above, the display portion 4 displays the endoscopic image 46 obtained from the image pickup device 12, and also displays the rotation angle display image data generated by the video processor 3 as the rotation angle display image 47 as shown in FIG. 6. Specifically, as shown in FIG. 6, coordinates 47a showing the up, down, left and right positions about the central axis O of the insertion portion 5, a circle 47b with the origin of the coordinates 47a as the center, a rotation limit line 47c showing the rotatable range about the origin of the coordinates 47a, and a point 47d, for example, as an indicator showing the rotation angle of the insertion portion 5 on the circle 47b, are displayed in the rotation angle display image 47. In the coordinates 47a, the up direction is the direction of the UP bending indicator 26a when viewing the central axis O from the upper side toward lower side of FIG. 2 (direction of the far side of the operation portion 6 viewed from the operator). Therefore, the character "UP" displayed on the rotation angle display image 47 indicates the angle corresponding to the neutral position of the rotation angle of the insertion portion 5.

Note that FIG. 6 shows one display example, and it is needless to say that another display manner may be employed. For example, when the insertion portion 5 is in the neutral position, at least one of a blinking display (of the point 47d, for example), a display (of the point 47d, for example) in a different displaying color, an additional display with characters indicating that the insertion portion is in the neutral position, and the like may be further performed. In this case, the neutral position can be perceived more definitely. Alternatively, the display portion 4 may be configured to be able to specify at least one arbitrary angle in the coordinates 47a (that is, may be configured to be able to specify two or more arbitrary angles), and when the rotation angle of the insertion portion 5 is at the specified angle, at least one of the blinking display, the display in a different displaying color, and the display with characters may be performed. In this case, the specified angle can be perceived more definitely.

According to the first embodiment, in addition to the endoscopic image 46, the rotation angle display image 47 is also displayed on the display portion 4 on which the endoscopic image 46 is displayed. Therefore, the operator can perceive an arbitrary rotation angle of the insertion portion 5 without looking away from the display portion 4. Accordingly, endoscopic examination can be performed more easily and rapidly.

In addition, the present embodiment provides a configuration for detecting the pressure as the physical quantity for calculating the rotation angle by using the deformation portion 41 made of an elastic material and the pressure sensor 42 in combination, thereby enabling a simple configuration and reduction in the production cost.

Since the elastic material for forming the deformation portion 41 can be selected from a wide variety of materials, an optimum material can be easily selected in accordance with endoscopes for various uses.

In addition, the present embodiment is a contact type in which the deformation portion 41 and the pressure sensor 42 contact each other, which provides an advantage of a less space required for arrangement.

Further, the physical quantity generation portion 13 and the detection portion 14 are provided at the insertion portion 5 and the operation portion 6, respectively. Therefore, compared with the case where the arrangement opposite to the above-described arrangement is employed, the present embodiment has an advantage of easy wiring. That is, the detection portion 14 has to be wired to the rotation angle calculation portion 15. However, the insertion portion 5 rotates with respect to the operation portion 6. Accordingly, if the detection portion 14 is disposed on the insertion portion 5 side, and the physical quantity generation portion 13 is disposed at the operation portion 6 side, a wiring structure has to be employed in which the electric connection from the detection portion 14 to the rotation angle calculation portion 15 can be maintained even if the insertion portion 5 rotates, which results in a complicated configuration. In contrast, employing the configuration according to the present embodiment enables such a complicated configuration to be avoided.

[Second Embodiment]

Figure 7:
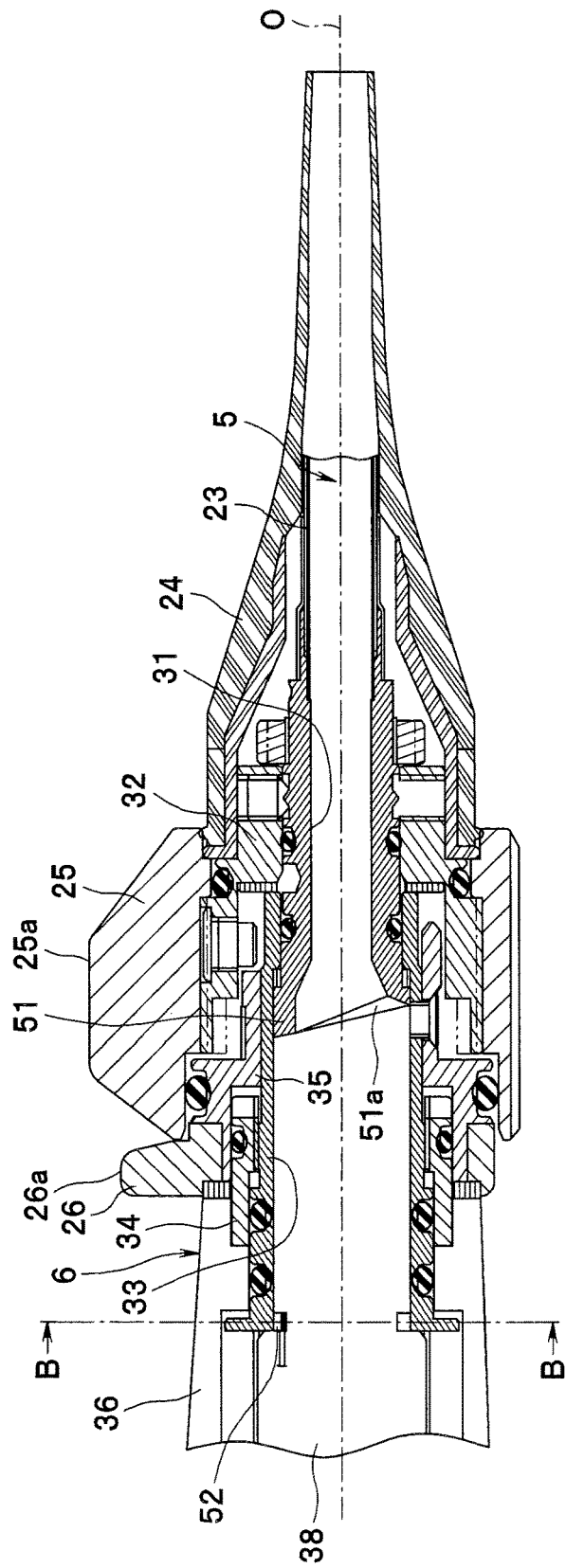
FIG. 7 is a cross-sectional view of a connecting part of an operation portion and an insertion portion according to a second embodiment of the present invention, taken along an axial direction.
Figure 8:
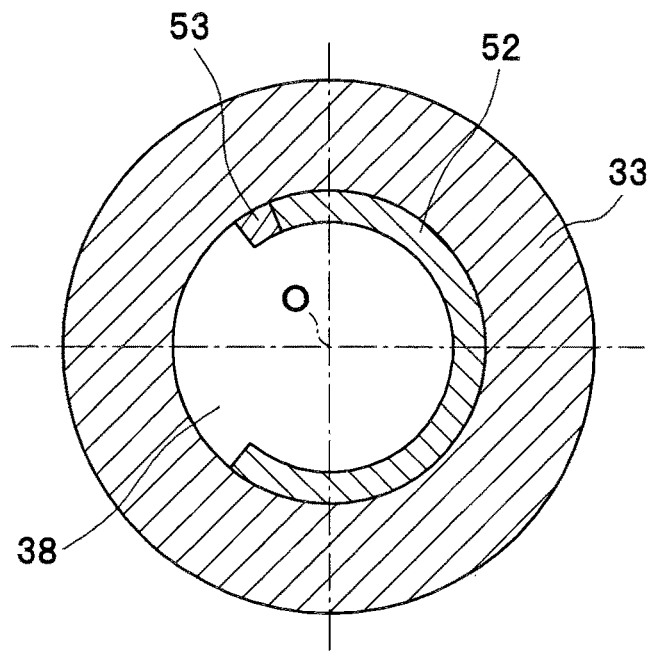
FIG. 8 is a cross-sectional view taken along the B-B line in FIG. 7 according to the second embodiment.

FIGS. 7 to 10 show the second embodiment of the present invention. FIG. 7 is a cross sectional view of the connecting part of the operation portion 6 and the insertion portion 5 taken along the axial direction, and FIG. 8 is a cross-sectional view taken along the B-B line in FIG. 7.

In the second embodiment, the parts which are same as those in the first embodiment are attached with the same reference numerals, and description thereof will be omitted. Only the different points will be mainly described.

In the above-described first embodiment, stress is detected as the physical quantity. On the other hand, a light-receiving position is detected in the present embodiment.

That is, as shown in FIG. 8, a light-emitting portion 53 that is capable of emitting a beam of spot light (laser light, for example) in the direction parallel to the central axis O of the insertion portion 5 is provided on the proximal end side, for example, of the inner circumferential surface of the operation portion collet 33 (See FIG. 7) according to the present embodiment.

Furthermore, on the inner circumferential surface of the operation portion collet 33 along the circumferential direction of the light-emitting portion 53, a light-receiving sensor 52, as a detection portion 14, that performs sensing of light in accordance with a light-receiving position is disposed in a circular-arc shape so as to be able to detect light in a predetermined angular range along the circumferential direction. The predetermined angular range is a range within which reflected light from a reflection surface 51a, to be described later, can be received.

On the other hand, on the proximal end surface of the insertion portion collet 31, a deformation portion 51 including the reflection surface 51a as a physical quantity generation portion 13 which reflects light from the light-emitting portion 53 to a different light-receiving position of the light-receiving sensor 52 depending on the rotation angle of the insertion portion 5 is provided. Therefore, more specifically, the light-emitting portion 53 emits light toward the reflection surface 51a of the deformation portion 51 (however, the light from the light-emitting portion 53 reaches a part of the reflection surface 51a, the axial direction position of the part being coincident with the axial direction position of the light-emitting portion 53. When the insertion portion 5 is rotated, the part of the reflection surface 51a where the light reaches also changes.)

Figure 9:
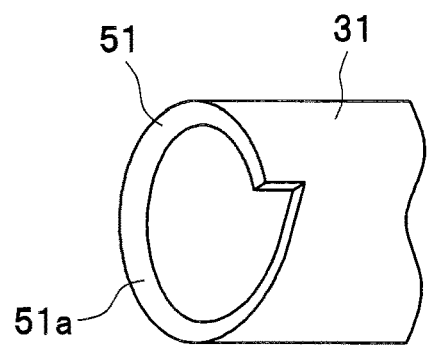
FIG. 9 is a perspective view showing a shape of a reflection surface of a deformation portion according to the second embodiment.

FIG. 9 is a perspective view showing the shape of the reflection surface 51a of the deformation portion 51.

As shown in FIG. 9, the reflection surface 51a is formed in a spiral shape such that the axial direction position about the central axis O of the insertion portion 5 changes at a certain rate, for example, depending on the angle about the central axis O. More specifically, the reflection surface 51a is provided slightly inclined so as to face the direction of the central axis O by the amount corresponding to the angle about the central axis O, thereby allowing the reflected light to reach (not the tangent line direction of the circumference when viewing the inner circumferential surface of the operation portion collet 33 from the direction of the central axis O but) an aimed angle position of the circular-arc shaped light-receiving sensor 52. The aimed angle position is a position where the longer the length of the optical path from the light-emitting portion 53 to the reflection surface 51a, the larger the angle about the central axis O from the light-emitting portion 53 to the light-receiving position on the light-receiving sensor 52.

Figure 10:
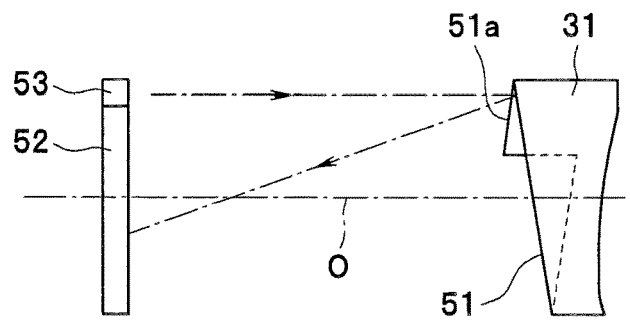
FIG. 10 is a side view showing an example of a position where reflected light reflected by the reflection surface of the deformation portion reaches a light-receiving sensor according to the second embodiment.

FIG. 10 is a side view showing an example of the position where the reflected light reflected by the reflection surface 51a of the deformation portion 51 reaches the light-receiving sensor 52.

During the use of the endoscope, the light-emitting portion 53 is caused to emit light in a blinking pattern at a certain time interval, for example. Description will be made on one light emission in the blinking pattern.

According to the configuration as described above, if the rotation angle of the insertion portion 5 with respect to the operation portion 6 changes, the length of the optical path from the light-emitting portion 53 to the reflection surface 51a changes, and the position on the reflection surface 51a where the light emitted from the light-emitting portion 53 is received and reflected changes. As a result, the position where the light-receiving sensor 52 receives the light reflected by the reflection surface 51*a* changes.

The rotation angle calculation portion 15 receives the light-receiving position at which the light-receiving sensor 52 performs sensing of light, to calculate the rotation angle of the insertion portion 5 on the basis of the received light-receiving position.

After that, similarly as in the above-described first embodiment, the display as shown in FIG. 6 is performed by the display portion 4 based on the calculated rotation angle.

According to the second embodiment thus configured, the light-emitting portion 53 and the light-receiving sensor 52 are arranged at the operation portion collet 33 and the deformation portion 51 including the reflection surface 51*a* is provided to the insertion portion collet 31, whereby capable of exhibiting substantially the same effects as those in the first embodiment.

In addition, the present embodiment is a non-contact type in which the deformation portion 51 and the light-receiving sensor 52 do not contact each other, to thereby eliminate friction. As a result, the present embodiment provides an advantage of high durability.

Using a sensor with high position detection accuracy as the light-receiving sensor 52 will result in high accuracy of the rotation angle to be calculated, which enables highly accurate angle detection to be performed.

Note that an image pickup device such as a CCD or a CMOS can be used as the light-receiving sensor 52. In this case, if the surface property (surface roughness, undulation, etc.) of the reflection surface 51*a* is rendered different depending on the rotation angle about the central axis O, the image obtained by the image pickup device is analyzed to obtain the surface property, to enable the rotation angle of the insertion portion 5 to be calculated based on the obtained surface property. Alternatively, instead of the surface property, the reflectivity of the reflection surface 51*a* may be rendered different depending on the angle about the central axis O, or when a color image pickup device is used, the color of the reflection surface 51*a* may be rendered different depending on the angle about the central axis O.

[Third Embodiment]

Figure 11:
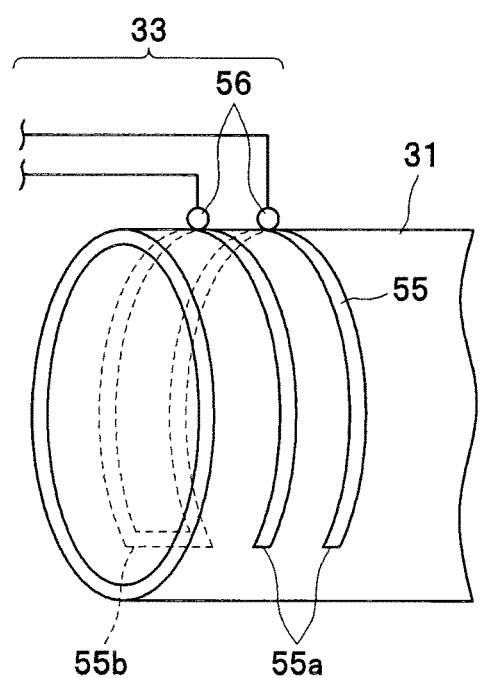
FIG. 11 is a perspective view showing a configuration of a main part of a connecting part of an operation portion collet and an insertion portion collet according to a third embodiment of the present invention.

FIG. 11 shows the third embodiment of the present invention, and is a perspective view showing a configuration of a main part of a connecting part of an operation portion collet 33 and an insertion portion collet 31.

In the third embodiment, the parts same as those in the first and second embodiments are attached with the same reference numerals and description thereof will be omitted. Only different points are mainly described.

In the present embodiment, a resistance value is detected as a physical quantity.

That is, as shown in FIG. 11, a resistive element 55 as a physical quantity generation portion 13 is provided on the outer circumferential surface of the insertion portion collet 31 according to the present embodiment, at a position where the outer circumference surface of the insertion portion collet 31 is slidable with respect to the inner circumferential surface of the operation portion collet 33.

The resistive element 55 is arranged along the circumferential direction of the insertion portion collet such that one linear resistor is folded back, with the center of the one linear resistor as a folded-back end 55*b*, and the folded-back linear resistor parts are arranged so as to be apart from each other with a certain interval in the axial direction, for example. Therefore, one end side of the resistive element 55 in the circumferential direction is the folded-back end 55*b*, and other end side is an open end 55*a*.

On the other hand, a pair of electric contacts 56 is provided on the inner circumferential surface of the operation portion collet 33 as a detection portion 14. The pair of the electric contacts 56 respectively contacts the one and the other of the folded-back linear resistor parts of the resistive element 55. The angular range in the circumferential direction, within which the above-described resistive element 55 is disposed, is configured to include an angular range within which the folded-back linear resistor parts can contact the electric contacts 56 (the angular range is substantially equal to the angular range within which the insertion portion 5 can be rotated with respect to the operation portion 6. See θ1, etc. in FIG. 5).

According to such a configuration, when the rotation angle of the insertion portion 5 with respect to the operation portion 6 changes, the length along the circumferential direction from the position where the pair of electric contacts 56 contacts the folded-back linear resistor parts to the folded-back end 55*b* changes. Therefore, the resistance value generated between the pair of electric contacts 56 by the resistive element 55 also changes depending on the rotation angle of the insertion portion 5.

The rotation angle calculation portion 15 in the video processor 3 detects the resistance value between the pair of electric contacts 56, to calculate the rotation angle of the insertion portion 5 based on the detected resistance value.

Note that the linear resistor which forms the resistive element 55 is not necessarily configured such that the resistance value per unit length is uniform in the length direction, but may be configured such that the resistance value per unit length increases (exponentially increases, for example) from the folded-back end 55*b* toward the open end 55*a*. In this case, since the change in the resistance value at the time when the rotation angle of the insertion portion 5 has changed becomes large, there is an advantage for reducing an angle detection error.

According to the third embodiment thus configured, the resistive element 55 is disposed at the insertion portion collet 31 and the electric contacts 56 are provided at the operation portion collet 33, whereby capable of exhibiting substantially the same effects as those of the above-described first and second embodiments.

In addition, the present embodiment allows the resistance value as the physical quantity to be detected by using the resistive element 55 and the electric contacts 56 in combination, which results in a simple configuration. In addition, since there is no need for providing a special sensor and the like, production cost can be reduced.

Since the material for forming the resistive element 55 can be selected from a wide variety of materials, an optimum material can be easily selected according to endoscopes for various uses.

Furthermore, the present embodiment is a contact type in which the resistive element 55 and the electric contacts 56 contact each other, which provides an advantage of less space required for arrangement.

Note that the stress, the light-receiving position (or surface property, reflectivity, or color), and the resistance value are used as the physical quantity to be detected in the first embodiment, the second embodiment, and the present embodiment, respectively. However, the physical quantity to be detected is not limited to the above, but another physical quantity, for example, time, current value, capacitance, light amount, strain amount, magnetism, temperature, acceleration, or the like may be used. Depending on which physical quantity is employed, the configuration of the physical quantity generation portion 13 on the insertion portion collet 31 side is also changed.

The physical quantity generation portion 13 disposed on the insertion portion 5 side is a deformation portion 41 whose outer diameter shape about the central axis O is not even in the first embodiment, and is the deformation portion 51 including the reflection surface 51a in the second embodiment. Both of these deformation portions do not require a supply of power. In addition, since the physical quantity generation portion is the resistive element 55 in the third embodiment, a voltage is applied for detecting a resistance value. However, the resistive element is different from an element (for example, sensor, or light-emitting element) which requires a driving power for causing the element to actively function. As described above, in order to facilitate the wiring, it is desirable for the physical quantity generation portion 13 disposed on the insertion portion 5 side to have a simpler configuration than that of the detection portion 14 disposed on the operation portion 6 side and not to require (at least active) power supply.

Figure 12:
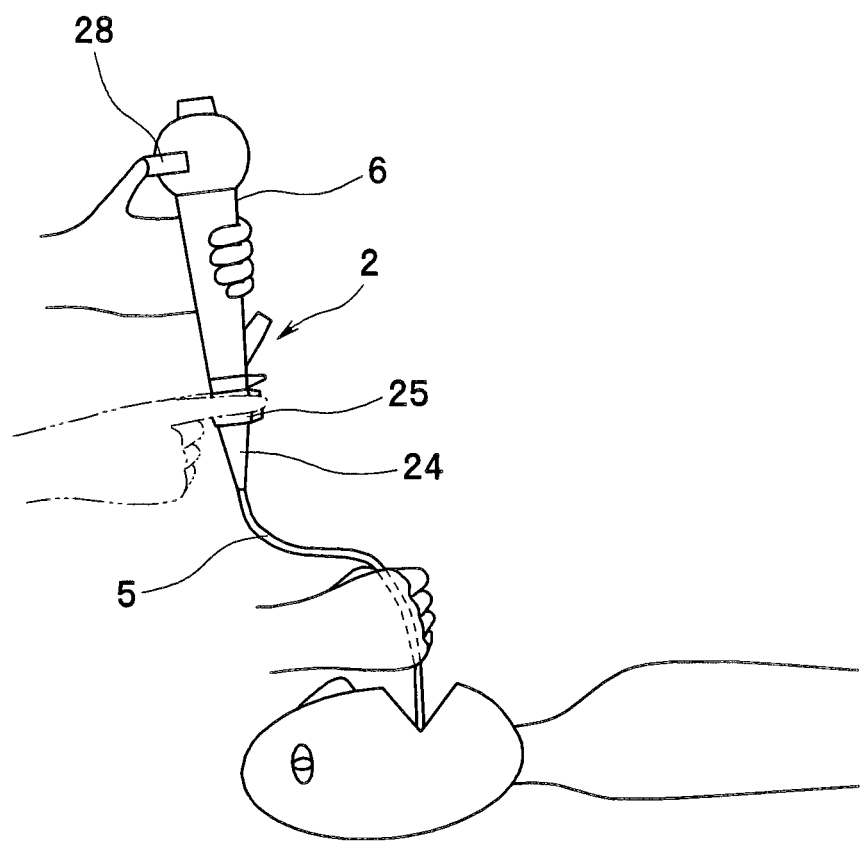
FIG. 12 illustrates a situation of an examination using a bronchoscope which relates to one example of an endoscope attachment which can be used in the endoscope system according to each of the above-described embodiments.
Figure 13:
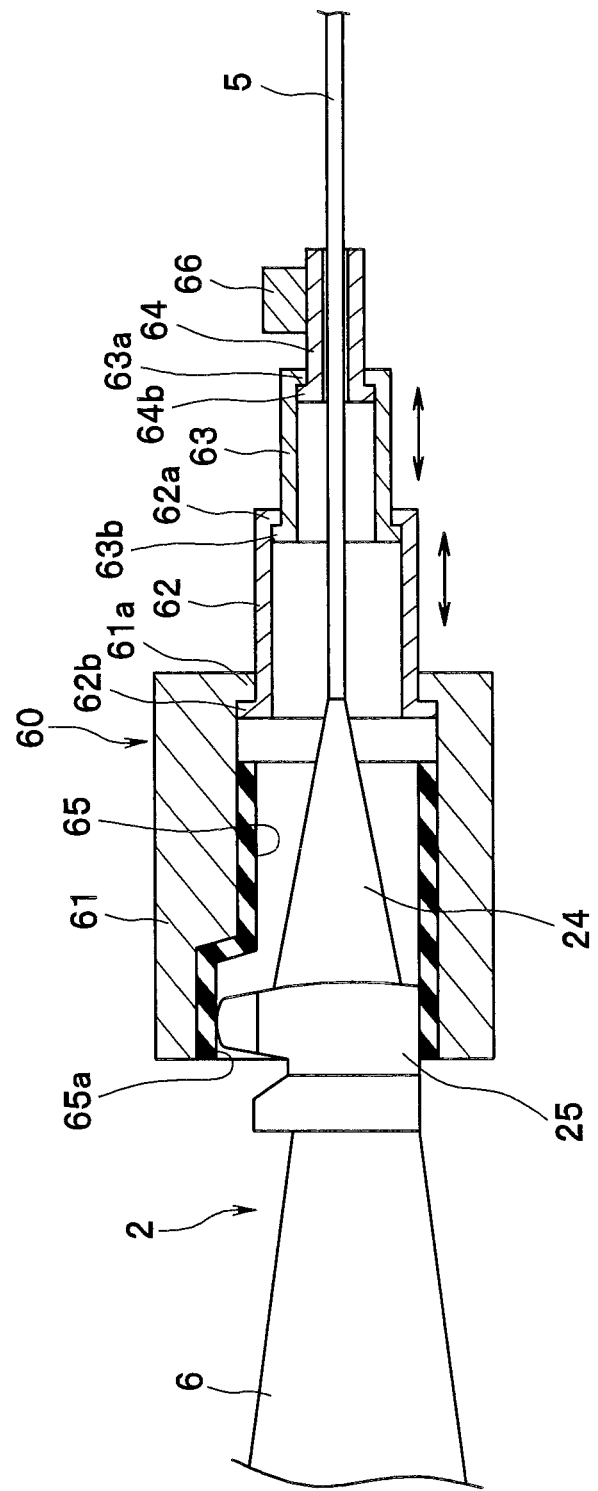
FIG. 13 is a cross-sectional view showing a configuration of an endoscope attachment attached to the endoscope, which relates to one example of the endoscope attachment which can be used in the endoscope system according to each of the above-described embodiments.
Figure 14:
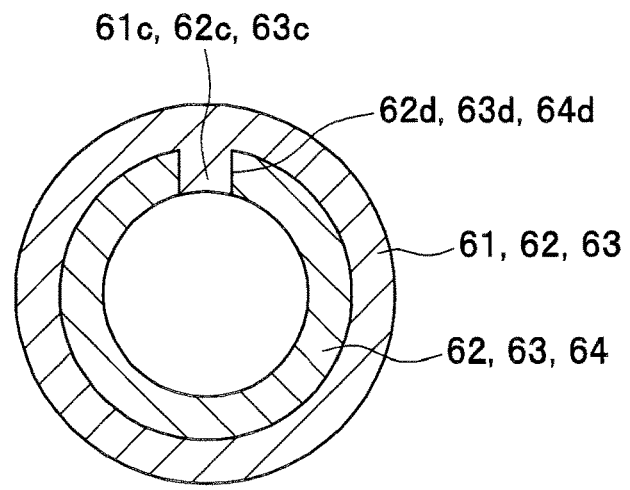
FIG. 14 is a cross-sectional view showing an appearance of keys and keyways of continuously provided cylindrical members, which relates to one example of the endoscope attachment which can be used in the endoscope system according to each of the above-described embodiments.

Next, with reference to FIGS. 12 to 14, description will be made on one example of an endoscope attachment which can be used in the electronic endoscope system 1 according to the respective embodiments. FIG.12 illustrates a situation of an examination using a bronchoscope, FIG. 13 is a cross-sectional view showing a configuration of an endoscope attachment attached to the endoscope 2, and FIG. 14 is a cross-sectional view showing an appearance of keys and keyways of continuously provided cylindrical members.

The endoscope 2, which has a mechanism in which the insertion portion 5 rotates with respect to the operation portion 6, is configured to rotate the insertion portion 5 by grasping and rotating the bend preventing portion 24 arranged between the operation portion 6 and the insertion portion 5 or the insertion portion rotating dial 25 provided on the proximal end side of the insertion portion 5, for performing rotation operation of the insertion portion 5.

The endoscope 2 thus configured is used for a bronchoscope in some cases, for example. When performing examination using a bronchoscope, the operator grasps the operation portion 6 with one hand to perform angle operation, and operates the bronchoscope while grasping the insertion portion 5 with the other hand at a position close to the patient's mouth, as shown in FIG. 12.

Accordingly, when rotating the insertion portion 5, the operator has to release the hand grasping the insertion portion 5 at the position close to the patient's mouth from the state of grasping the insertion portion 5, to move the hand to the insertion portion rotating dial 25 or the bend preventing portion 24, and then regrasp the insertion portion rotating dial or the bend preventing portion to perform rotation operation.

Therefore, when performing the rotation operation, the operator has to release the hand grasping the insertion portion 5, which results in unstable operation. In addition, the operator has to move the hand grasping the insertion portion from the position close to the patient's mouth to the insertion portion rotating dial 25 or the bend preventing portion 24, which results in a complicated operation.

The endoscope attachment 60 has a configuration achieved in view of the above-described points.

The endoscope attachment 60 is configured as an extendable/contractable multi-stage cylindrical member which includes a proximal-end-side first cylindrical member 61 and including on the inner circumferential side thereof an elastic engaging portion 65 to be engaged with the insertion portion rotating dial 25 so as to rotationally move integrally with the insertion portion rotating dial, and a plurality of cylindrical members (in the example shown in FIG. 13, second to fourth cylindrical members 62 to 64) continuously provided from the first cylindrical member 61 toward the distal end side and configured to rotationally move integrally with the first cylindrical member 61 and to be movable in the longitudinal direction of the insertion portion 5.

Specifically, the first cylindrical member 61 is configured so as to be disposed on the outer circumferential side of the insertion portion rotating dial 25 and the bend preventing portion 24, and the elastic engaging portion 65 on the inner circumferential side has an inner surface shape portion 65a which has a shape substantially coincide with the outer shape of the insertion portion rotating dial 25. The elastic engaging portion 65 is made of an elastic material such as rubber, and configured to prevent a useless clearance from being created as much as possible, when the inner surface shape portion 65a is engaged with the insertion portion rotating dial 25, that is, prevent generation of backlash at the time of rotational movement operation. In addition, since the elastic engaging portion 65 is made of an elastic material, a friction force is generated between the elastic engaging portion and the insertion portion rotating dial 25 at the time of rotational movement operation, which enables the gripping force to be increased. According to such a configuration, when the endoscope attachment 60 is attached to the endoscope 2, the first cylindrical member 61 and the insertion portion rotating dial 25 rotationally move together in an integrated manner. In addition, at the distal end portion of the first cylindrical member 61, an inward flange 61a is formed.

On the distal end side of the inner circumference of the first cylindrical member 61, the second cylindrical member 62 which has an outer circumferential diameter substantially the same as the inner circumferential diameter of the first cylindrical member 61 (more accurately, the outer circumferential diameter slightly smaller than the inner circumferential diameter of the first cylindrical member 61) is disposed. On the proximal end side of the second cylindrical member 62, an outward flange 62b is formed, and the outward flange is engaged with the inward flange 61a of the first cylindrical member 61, thereby preventing the second cylindrical member from falling off in the axial direction.

Similarly, also on the distal end side of the second cylindrical member 62, the third cylindrical member 63 and the fourth cylindrical member 64, diameters of which become smaller in this order, are disposed (Note that four cylindrical members are provided continuously in the example shown in FIG. 13. However, it is needless to say that the number of the cylindrical members is not limited to four.)

Note that outward flanges 63b, 64b, which have the same function as that of the outward flange 62b of the second cylindrical member 62, are also formed on the proximal end sides of the third cylindrical member 63 and the fourth cylindrical member 64, respectively. In addition, inward flanges 62a, 63a, which have the same function as that of the inward flange 61a of the first cylindrical member 61, are formed also on the distal end sides of the second cylindrical member 62 and the third cylindrical member 63, respectively, except for the fourth cylindrical member 64 located on the distal-most side.

As shown in FIG. 14, for example, the above-described cylindrical members 61 to 64 are joined to each other such that the key of one of the two cylindrical members continuously provided is engaged with the keyway of the other of the two cylindrical members, and the key and the keyway are provided so as to be parallel to the extending/contracting direction of the endoscope attachment 60. Specifically, in the example shown in FIG. 14, a key 61c (62c, or 63c) is protrudedly provided on the inner circumferential side of the cylindrical member 61 (62 or 63) located on the outer circumferential side, and the cylindrical member 62 (63 or 64) located on the inner circumferential side includes a keyway 62d (63d, or 64d) formed so as to receive the key 61c (62c, or 63c). Note that the key and the keyway are not limited to one line, but it is needless to say that a plurality of lines of keys and keyways may be provided.

According to such a configuration, the keys 61c, 62c, and 63c and the keyways 62d, 63d, and 64d maintain all of the cylindrical members 61 to 64 so as to rotationally move in an integrated manner, without interfering with the extending/contracting action of the endoscope attachment 60 constituted of a plurality of cylindrical members 61 to 64.

Since the fourth cylindrical member 64 located on the distal-most side has the smallest diameter among the plurality of cylindrical members 61 to 64, a certain amount of force is required to rotate the fourth cylindrical member 64 by grasping the outer circumferential surface thereof. Therefore, as shown in FIG. 13, a protruding portion 66 which protrudes in the outer radial direction is provided to enable the fourth cylindrical member to rotate easily with a small amount of force.

The endoscope attachment 60 thus configured is brought into a contracted state, for example, before performing endoscopic examination, to be inserted from the distal end side of the insertion portion 5, and the elastic engaging portion 65 of the first cylindrical member 61 is engaged with the insertion portion rotating dial 25.

When performing operation such as insertion of the endoscope 2, the operator performs operation while extending or contracting the endoscope attachment 60 such that the distal-most fourth cylindrical member 64 is always located close to the patient's mouth.

Using the endoscope attachment 60 as shown in FIGS. 13 and 14 enables the operator to perform rotation operation of the insertion portion 5 while maintaining the state of grasping the insertion portion 5 at the position close to the patient's mouth. Therefore, such an endoscope attachment is capable of preventing unstable operation and reducing complication of the operation.

Figure 15:
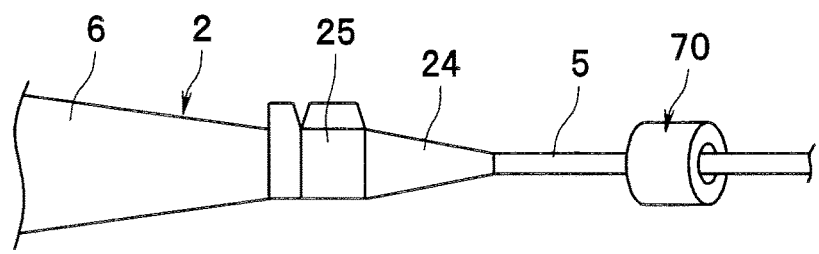
FIG. 15 illustrates a configuration of an endoscope attachment attached to the endoscope, which relates to another example of the endoscope attachment which can be used in the endoscope system according to each of the above-described embodiments.

Next, with reference to FIGS. 15 and 16, description will be made on another example of an endoscope attachment which can be used in the electronic endoscope system 1 according to the above-described embodiments. FIG. 15 illustrates the configuration of the endoscope attachment attached to the endoscope 2, and FIG. 16 is a cross-sectional view perpendicular to the central axis O, which illustrates the configuration of the endoscope attachment.

Figure 16:
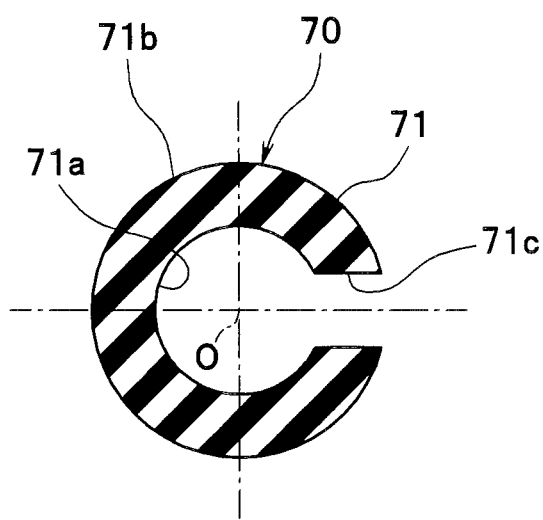
FIG. 16 is a cross-sectional view perpendicular to a central axis showing a configuration of an endoscope attachment, which relates to another example of the endoscope attachment which can be used in the endoscope system according to each of the above-described embodiments.

An endoscope attachment 70 as shown in FIGS. 15 and 16 shows another exemplary configuration for solving the problem same as the problem to be solved by the endoscope attachment 60 as shown in FIGS. 12 to 14.

The endoscope attachment 70 is a member whose cross section perpendicular to the central axis O is a C-shape as shown in FIG. 16, and the endoscope attachment 70 is provided with a cylindrical member 71 made of an elastic material and including an inner circumferential surface 71a which has an inner diameter larger than the outer diameter of the insertion portion 5, and a notch 71c provided so as to be parallel to the central axis O at a part of the circumferential direction of the cylindrical member 71.

The inner circumferential surface 71a of the endoscope attachment 70 is formed so as to have a diameter somewhat larger than the diameter of the outer circumferential surface of the insertion portion 5. In addition, the endoscope attachment 70 is formed so as to have a predetermined thickness such that the outer circumferential surface 71b has an outer diameter of a size which does not require a large amount of force for rotation operation (In other words, also the insertion portion 5 of the endoscope 2 is set to have an amount of rotational force for allowing the rotation operation to be performed with the endoscope attachment 70).

The endoscope attachment 70 thus configured is attached to the insertion portion 5 from the lateral side through the cutout 71c when an endoscopic examination is performed. Since the endoscope attachment 70 is made of an elastic material, the shape of the endoscope attachment deforms appropriately at the time of the attachment, for example, the cutout 71c opens, which enables easy attachment.

When inserting the endoscope 2, the operator moves the endoscope attachment 70 along the insertion portion 5 such that the endoscope attachment 70 is always located close to the patient's mouth. When moving the endoscope attachment 70, if the operator relaxes the force grasping the endoscope attachment 70, the endoscope attachment 70 can move easily, since the diameter of the inner circumferential surface 71a of the endoscope attachment 70 is larger than the diameter of the outer circumferential surface of the insertion portion 5.

On the other hand, when rotating the insertion portion 5, the operator grasps the endoscope attachment 70 with an appropriate amount of force, thereby bringing the inner circumferential surface 71a into contact with the outer circumferential surface of the insertion portion 5. Then, the pressing force with which the inner circumferential surface 71a of the endoscope attachment 70 presses the outer circumferential surface of the insertion portion 5 causes a frictional force to be generated between the endoscope attachment 70 and the insertion portion 5. This frictional force enables the endoscope attachment 70 and the insertion portion 5 to rotate so as to rotationally move together in an integrated manner At the time of the rotation, the rotation can be easily performed with a small amount of force, since the outer diameter of the endoscope attachment 70 is larger than the outer diameter of the insertion portion 5.

With the endoscope attachment 70 as shown in FIGS. 15 and 16, rotation operation of the insertion portion 5 is possible while maintaining the state where the insertion portion 5 is grasped at the position close to the patient's mouth. Such a configuration prevents unstable operation and reduces the complication of the operation.

In addition, the endoscope attachment 70 shown in FIGS. 15 and 16 is configured to be attached to and detached from the insertion portion with the use of the cutout 71c. Therefore, the endoscope attachment 70 may be attached to the insertion portion 5 before performing endoscopic examination, or can be attached to and detached from the insertion portion as desired when needed during the endoscopic examination. Such a configuration provides an advantage of user-friendliness.

In addition, the endoscope attachment 70 is made of an elastic material and formed in a relatively simple shape, which enables the production cost to be greatly reduced.

Note that the present invention is not limited to the above-described embodiments as they are, and can be embodied by modifying the constituent elements in the practical phase without departing from the gist of the invention. In addition, various aspects of the invention can be formed by appropriately combining a plurality of constituent elements disclosed in the embodiments. For example, some constituent elements can be deleted from all of the constituent elements disclosed in the embodiments. Furthermore, constituent elements in different embodiments may be appropriately combined. Thus, it is needless to say that various changes and modifications are possible without departing from the gist of the invention.

What is claimed is:

1. An electronic endoscope system comprising:
an operation portion configured to be operable by an operator;
an insertion portion including on a distal end side thereof a bending portion, configured to be bendable only in two directions, the two directions being one direction and a direction opposite to the one direction, the insertion portion being connected to the operation portion so as to be rotatable with respect to the operation portion, a bending direction of the bending portion changing depending on rotation of the insertion portion;
an image sensor disposed in the insertion portion and configured to generate an electronic image by photoelectrically converting an optical image of a subject;
a physical quantity generation portion configured to generate a physical quantity which changes depending on the rotation of the insertion portion;
a detection portion configured to detect the physical quantity generated by the physical quantity generation portion and output the detected physical quantity; and
a processor comprising hardware, wherein the processor is configured to:
receive the physical quantity outputted from the detection portion and calculate a rotation angle of the insertion portion; and
control a display to display the image of the subject generated by the image sensor and information generated based on the calculated rotation angle, the information corresponding to the rotation angle of the insertion portion,
wherein the information corresponding to the rotation angle, which is displayed on the display, is information indicating the one direction with respect to coordinates, and
wherein the coordinates indicates up, down, left, and right positions around a central axis of the insertion portion at a time when the rotation angle of the insertion portion is in a neutral position.

2. The electronic endoscope system according to claim 1, wherein the physical quantity generation portion is provided at the insertion portion and the detection portion is provided at the operation portion.

3. The electronic endoscope system according to claim 1, wherein the physical quantity generation portion includes a deformation portion that is formed such that a shape about the central axis of the insertion portion changes depending on an angle about the central axis.

4. The electronic endoscope system according to claim 3, wherein the operation portion comprises an operation portion collet,
wherein the insertion portion comprises an insertion portion collet fitted to the operation portion collet so that the insertion portion is rotatable with respect to the operation portion,
wherein the detection portion is disposed at the operation portion collet, and
wherein the deformation portion is disposed at the insertion portion collet.

5. The electronic endoscope system according to claim 4,
wherein the deformation portion is made of an elastic material such that a diameter about the central axis of the insertion portion changes depending on the angle about the central axis,
wherein the detection portion includes a pressure sensor that is provided at the operation portion collet so as to contact the deformation portion and detects a pressure applied by the deformation portion depending on the rotation angle of the insertion portion, and
wherein the processor is configured to calculate the rotation angle of the insertion portion based on the pressure detected by the pressure sensor.

6. The electronic endoscope system according to claim 4, further comprising a light source that is disposed at the operation portion collet, wherein the light source is configured to emit light toward the deformation portion,
wherein the detection portion includes a light-receiving sensor configured to sense light in accordance with a light-receiving position,
wherein the deformation portion comprises a reflection surface that reflects the light emitted from the light source to a different light-receiving position of the light-receiving sensor depending on the rotation angle of the insertion portion, and
wherein the processor is configured to calculate the rotation angle of the insertion portion based on the light-receiving position at which the light-receiving sensor performs sensing of light.

7. The electronic endoscope system according to claim 1,
wherein the detection portion includes a pair of electric contacts,
wherein the physical quantity generation portion includes a resistive element that is disposed so as to slidably contact the pair of electric contacts, the resistive element generating a different resistance value between the pair of electric contacts depending on the rotation angle of the insertion portion, and
wherein the processor is configured to calculate the rotation angle of the insertion portion based on the resistance value detected through the pair of electric contacts.

8. The electronic endoscope system according to claim 7,
wherein the operation portion and the insertion portion are configured to be rotatable by fitting an operation portion collet provided at the operation portion and an insertion portion collet provided at the insertion portion to each other,
wherein the pair of electric contacts are disposed at the operation portion collet, and
wherein the resistive element is disposed at the insertion portion collet.

9. The electronic endoscope system according to claim 1,
wherein the processor is configured to control the display to:
use up, down, left and right positions about the central axis of the insertion portion as coordinates, and
display an indicator which indicates the rotation angle of the insertion portion on the coordinates.

10. The electronic endoscope system according to claim 9, further comprising a bending operation portion provided at the operation portion,
wherein the processor is configured to control the display to perform at least one of a blinking display, a display in a different displaying color, and a display with characters, when the rotation angle of the insertion portion is at an angle corresponding to a neutral position at which a bending operation direction of the bending operation portion and a bending direction of the bending portion coincide with each other.

11. The electronic endoscope according to claim 9, further comprising a bending operation portion provided at the operation portion,
wherein the processor is configured to control the display to specify at least one arbitrary angle in the coordinates, and perform at least one of a blinking display, a display in different displaying color, and a display with characters, when the rotation angle of the insertion portion is at the specified angle.

12. The electronic endoscope system according to claim 1,
wherein an insertion portion rotating dial for performing rotation operation of the insertion portion is provided on a proximal end side of the insertion portion, and
the electronic endoscope system further includes an endoscope attachment constituted of an extendable and contractable multi-stage cylindrical member, the endoscope attachment including a proximal-end-side cylindrical member which includes an elastic engaging portion for allowing the proximal-end-side cylindrical member to engage with the insertion portion rotating dial so as to rotationally move integrally with the insertion portion rotating dial, and a plurality of cylindrical members provided continuously from the proximal-end-side cylindrical member toward a distal end side and configured to rotationally move integrally with the proximal-end-side cylindrical member and to be movable in a longitudinal direction of the insertion portion.

13. The electronic endoscope system according to claim 1, further comprising an endoscope attachment having a C-shaped cross section perpendicular to the central axis,
wherein the endoscope attachment comprises:
a cylindrical member comprising an elastic material and having an inner diameter larger than an outer diameter of the insertion portion,
wherein the cylindrical member defines a cutout provided in parallel with the central axis at a part of a circumferential direction of the cylindrical member.

* * * * *